United States Patent [19]

Kalbfeld et al.

[11] Patent Number: 5,503,266

[45] Date of Patent: Apr. 2, 1996

[54] MOLDED SUTURE RETAINER WITH NEEDLE PARK

[75] Inventors: Russell G. Kalbfeld, North Haven; Christopher Scanlon, Milford; Hans-Jurgen F. Sinn, deceased, late of Fairfield, all of Conn.

[73] Assignee: United States Surgical Corporation, Norwalk, Conn.

[21] Appl. No.: 137,325

[22] Filed: Oct. 15, 1993

(Under 37 CFR 1.47)

[51] Int. Cl.$^6$ .................................................. A61B 17/06
[52] U.S. Cl. ........................................ 206/63.3; 206/380
[58] Field of Search ................................. 206/63.3, 227, 206/380, 388, 443, 475

[56] References Cited

U.S. PATENT DOCUMENTS

| | | |
|---|---|---|
| 3,136,418 | 6/1964 | Stacy et al. . |
| 3,280,971 | 10/1966 | Regan, Jr. . |
| 3,338,401 | 8/1967 | Regan, Jr. . |
| 3,490,192 | 1/1970 | Regan, Jr. . |
| 3,545,608 | 12/1970 | Berger et al. . |
| 3,627,120 | 12/1971 | Bordeau . |
| 3,759,376 | 9/1973 | Lisowski . |
| 3,768,635 | 10/1973 | Eggert . |
| 3,876,068 | 4/1975 | Sonnino . |
| 3,959,947 | 6/1976 | Sonnino . |
| 3,972,418 | 8/1976 | Schuler et al. . |
| 4,034,850 | 7/1977 | Mandel et al. . |
| 4,063,638 | 12/1977 | Marwood . |
| 4,151,913 | 5/1979 | Freitag .................. 206/63.3 |
| 4,183,431 | 1/1980 | Schmidt et al. . |
| 4,235,563 | 3/1981 | Komarnycky . |
| 4,249,656 | 2/1981 | Cerwin et al. . |
| 4,406,363 | 9/1983 | Aday . |
| 4,412,613 | 11/1983 | Kubas . |
| 4,412,614 | 11/1983 | Ivanou et al. . |
| 4,424,898 | 1/1984 | Thyen et al. . |
| 4,427,109 | 1/1984 | Roshdy . |
| 4,496,045 | 1/1985 | Ferguson et al. . |
| 4,573,575 | 3/1986 | Bergrath et al. . |
| 4,574,948 | 3/1986 | Huck et al. . |
| 4,699,271 | 10/1987 | Lincoln et al. . |
| 4,802,581 | 2/1989 | Takahashi . |
| 4,961,498 | 10/1990 | Kalinski et al. . |
| 4,967,902 | 11/1990 | Sobel et al. . |
| 5,048,678 | 9/1991 | Chambers . |
| 5,052,551 | 10/1991 | Cerwin et al. . |
| 5,056,658 | 10/1991 | Sobel et al. . |
| 5,078,730 | 1/1992 | Li et al. . |
| 5,099,994 | 3/1992 | Kalinski et al. . |
| 5,101,968 | 4/1992 | Henderson et al. . |
| 5,123,528 | 6/1992 | Brown et al. . |
| 5,131,533 | 7/1992 | Alpern . |
| 5,154,283 | 10/1992 | Brown . |
| 5,192,483 | 3/1993 | Kilgrow et al. . |
| 5,301,801 | 4/1994 | Sinn .................. 206/63.3 |

FOREIGN PATENT DOCUMENTS

| | | | |
|---|---|---|---|
| 2536924 | 3/1976 | Germany | 206/63.3 |
| 2161130 | 1/1986 | United Kingdom . | |

*Primary Examiner*—Jimmy G. Foster

[57] ABSTRACT

A suture retainer for storing at least one suture having a needle attached thereto comprises a molded base panel having a passageway formed therein for accommodating a suture portion, a cover sheet affixed to the molded base panel to enclose the passageway and at least one needle holding park integrally formed with the molded base panel and extending through at least one opening formed in the cover sheet. The needle holding park defines a groove dimensioned and configured to receive a suture needle and frictionally engage the outer surfaces of the needle to secure the needle to the retainer.

18 Claims, 5 Drawing Sheets

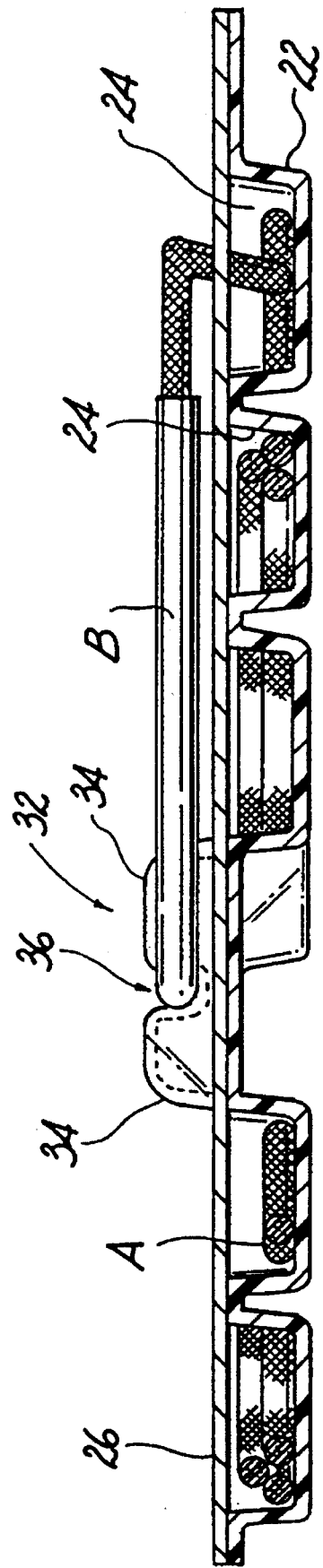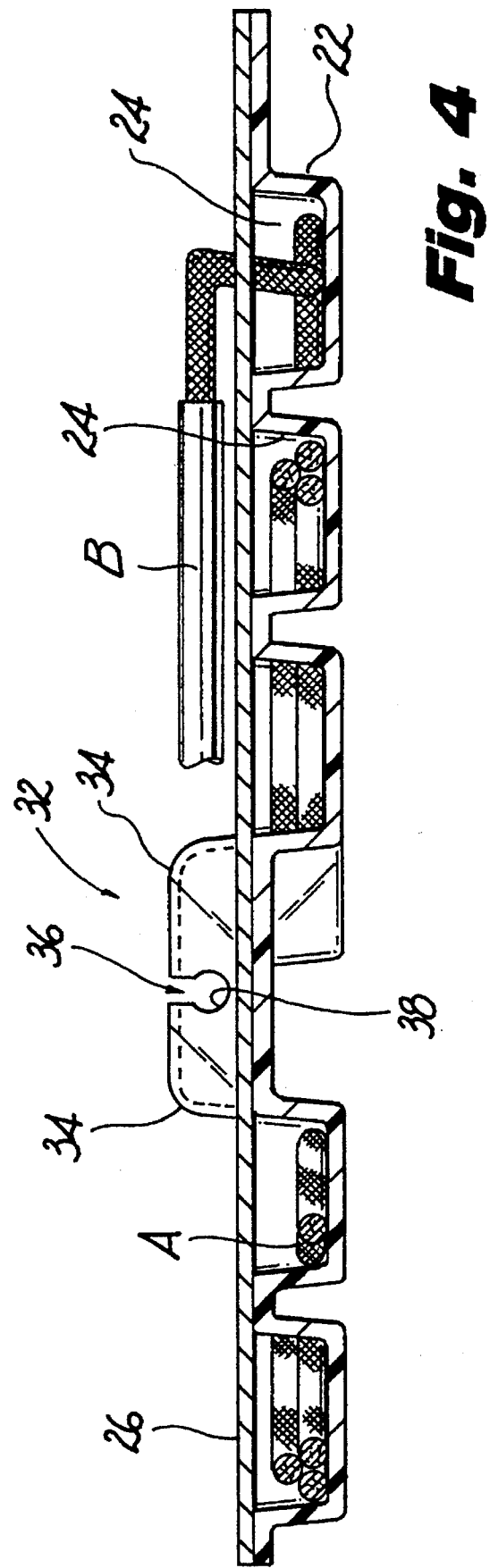

MOLDED SUTURE RETAINER WITH NEEDLE PARK

BACKGROUND OF THE INVENTION

1. Field of the Invention

The present invention relates to a retainer package for surgical sutures, and, more particularly, to a molded retainer incorporating a novel needle park for securely retaining one or more surgical needles.

2. Description of the Prior Art

Many types of retainers for surgical sutures and suture-needle assemblies are well known in the art. Generally, a retainer should be constructed to adequately secure a needle and suture while providing easy withdrawal during use. It is also preferable to minimize the formation of kinks or bends in the suture during storage.

A first type of known retainer consists of a series of panels interconnected to each other along score lines. The panels are adapted to fold onto each other to enclose a suture packaged therein. Typically, the suture is wound in an oval or figure "8" pattern within the retainer. The needle may be secured in a slot or die cut formed in one of the panel members, or in the alternative, may piercingly engage a foam strip affixed to a panel member.

Another type of retainer is of molded construction such as the retainer disclosed in U.S. Pat. No. 5,154,283 to Brown. The retainer described in the Brown '283 patent includes a molded cover member having a spiraled passageway formed therein to accommodate a suture and a cover sheet adhered to the molded member to close the passageway. The passageway is characterized by defining a relatively wide channel having a width several times the diameter of the suture disposed therein. A significant feature of this package is that the sutures stored therein exhibit fewer kinks and bends as compared to prior suture packages.

Although the Brown '283 patent has proved to be extremely effective in storing sutures and minimizing the formation of kinks or bends in the suture during storage, the present invention relates to further improvements whereby a molded retainer incorporates a novel needle park to retain the needle in an effective and secure manner while providing easy withdrawal during use.

SUMMARY OF THE INVENTION

A suture retainer comprises a molded base panel having a passageway formed therein for reception of a suture portion, a cover sheet affixed to the molded base panel to enclose the passageway and needle holding means extending generally transversely relative to a plane defined by the base panel through an opening formed in the cover sheet for securably engaging a needle attached to the suture portion.

The needle holding means comprises a needle park integrally formed with the molded base panel and defining a needle receiving channel dimensioned to receive and accommodate the needle therein. The needle receiving channel is configured in a manner such that portions of the needle park defining the needle receiving channel frictionally engage the outer surfaces of the needle to secure the needle to the needle park.

In an alternative preferred embodiment, the molded needle park comprises at least two projecting members extending generally transversely relative to a plane defined by the molded base panel. The projecting members define the needle receiving channel therebetween and may be positioned to frictionally engage the needle received within the needle receiving channel. Each projecting member has a lip portion formed contiguous therewith. The lip portions extend generally inwardly towards the center of the needle receiving channel and are particularly oriented to engage the needle to retain the needle within the receiving channel.

The molded base panel of the preferred retainer comprises a moldable transparent plastic material while the cover sheet is constructed of a spun bonded polyolefin. The cover sheet includes a suture receiving port to permit access to a suture receiving section of the passageway of the base panel and a vacuum port aligned with a vacuum receiving section of the passageway. The suture retainer may also comprise a needle cover panel foldably attached to the cover sheet and adapted to fold onto the needle within the needle holding means.

The present invention is also directed to a suture retainer for storing at least one suture having a needle attached thereto, comprising a molded base panel having a passageway formed therein for accommodating a suture portion, a cover sheet affixed to the molded base panel to enclose the passageway and at least one needle holding park integrally formed with the molded base panel and extending through at least one opening formed in the cover sheet. The needle park defines a groove therein dimensioned and configured to receive a suture needle and frictionally engage the outer surfaces of the needle to secure the needle to the retainer.

The present invention is further directed to a needle park for retaining at least one surgical needle in a suture retainer. The needle park comprises a base panel having two projecting members extending generally transversely relative to a plane defined by the base panel and defining a needle receiving channel therebetween for accommodating a needle. The projecting members each have a lip portion formed contiguous therewith which extend generally inwardly towards the center of the receiving channel. The lip portions are oriented in a manner to at least partially enclose the channel and retain the needle against the base panel.

BRIEF DESCRIPTION OF THE DRAWINGS

The accompanying drawings, referred to herein and constituting a part hereof, illustrate the preferred embodiments of the present invention, and together with the description serve to explain the principles of the invention, wherein:

FIG. 3 is a cross-sectional view taken along the lines 3—3 of FIG. 1 illustrating securement of the needle in the needle park;

FIG. 4 is a view similar to the cross-sectional view of FIG. 3 illustrating an alternative needle park having a generally arcuate channel portion for accommodating the needle;

DETAILED DESCRIPTION OF THE PREFERRED EMBODIMENTS

Figure 1:
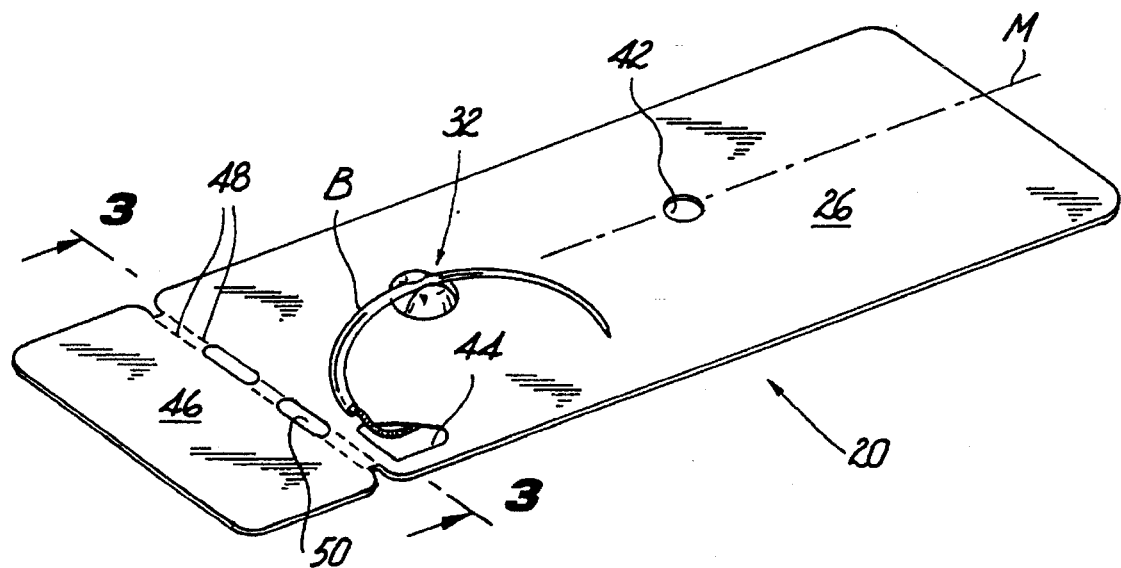
FIG. 1 is a perspective view of a preferred embodiment of a suture retainer constructed in accordance with the present invention.

Referring initially to FIG. 1, there is illustrated in perspective view the suture retainer 20 constructed according to the present invention. Retainer 20 is similar to the retainer disclosed in U.S. Pat. No. 5,154,283 to Brown, the contents of which are incorporated herein by reference. Retainer 20 is particularly adapted to accommodate a double or triple folded suture in a suture compartment defined by the retainer, and to retain a needle attached to the suture in a readily accessible position adjacent the retainer.

Figure 2:
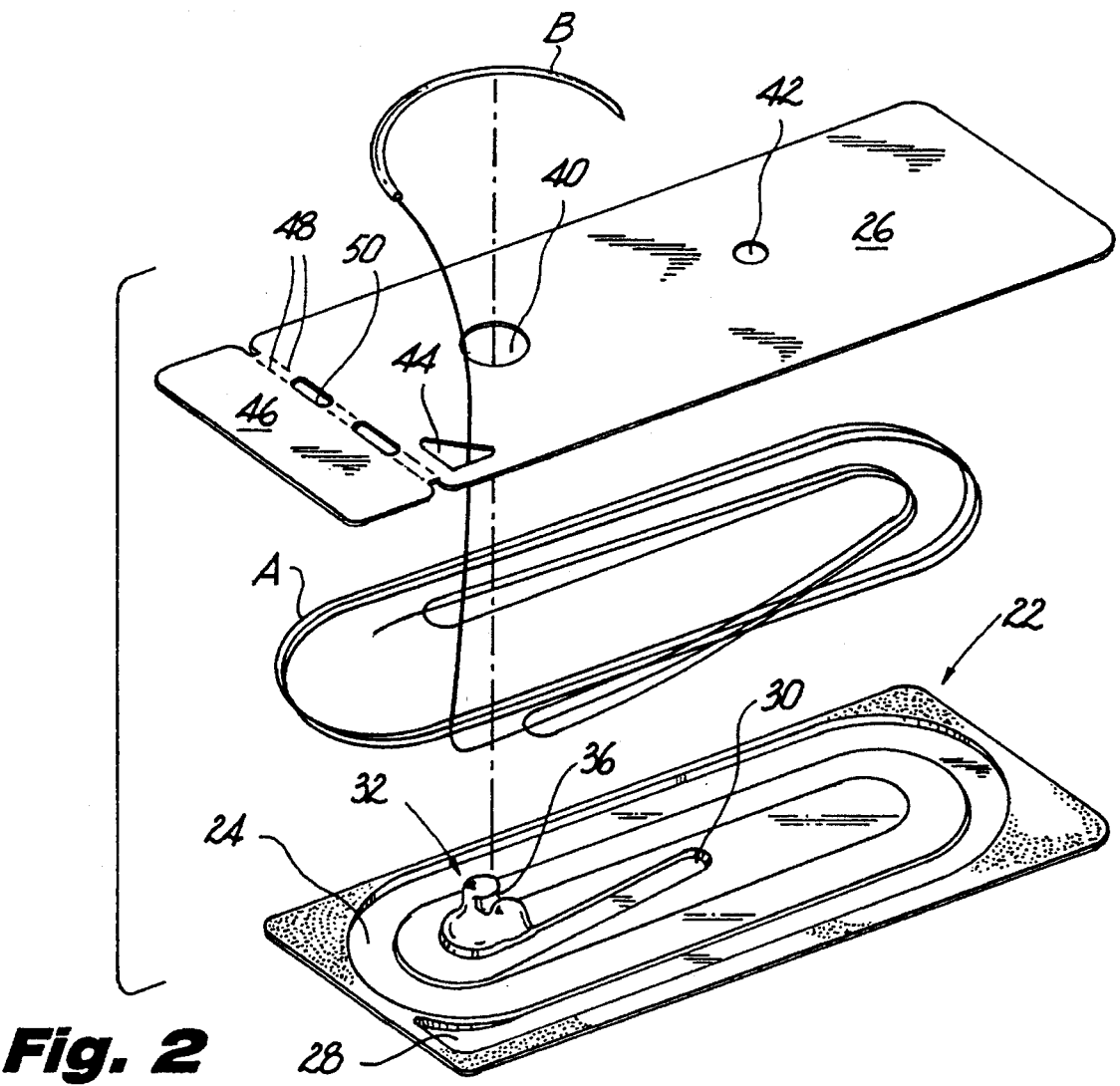
FIG. 2 is a perspective view with parts separated of the suture retainer of FIG. 1 illustrating the base panel with the needle park integrally formed therewith, a suture in a coiled configuration and the cover sheet.

Referring now to FIGS. 1–3, retainer 20 includes base panel 22 having passageway 24 formed therein for accommodating suture A in a coiled configuration and a cover sheet 26 for enclosing the passageway. Passageway 24 is characterized in that it possesses a minimal number of convolutions. The passageway 24 follows a generally oval pattern commencing at peripheral suture receiving section 28 and spiraling toward the proximate center through several turns while terminating at a central vacuum receiving section 30.

Base panel 22 is fabricated from a moldable transparent plastic material such as, for example, polyethylene teraphthalate (PETG), of Eastman Kodak 6763. Other materials suitable for base panel 22 include polyvinylchloride, polyethylene, polypropylene and high impact polystyrene. Base panel 22 is approximately 3.350 inches (85.09 millimeters) by 1.375 inches (34.925 millimeters) in order to conform to commonly accepted overall dimensions of conventional suture packages and display boxes. The retainers are preferably about 0.010 inches (0.254 millimeters) thick.

A needle park identified by reference numeral 32 extends generally transversely from base panel 22 along the general midline M of the panel 22 (FIG. 1). As best depicted in FIG. 3, needle park 32 includes two transverse members 34 which define a needle receiving channel 36 therebetween. Needle channel 36 is strategically dimensioned to receive and accommodate a needle B therein, and to securely retain the needle B against cover sheet 26 in the manner shown in FIG. 1. In a preferred embodiment, transverse members 34 are positioned to frictionally engage portions of the inner and outer surfaces of needle B as shown in FIG. 3. Transverse portions 34 may also be slightly resilient and capable of deforming to the outer contours of needle B. In an alternative embodiment shown in FIG. 4, needle receiving channel 36 may possess a lower base portion 38 of generally arcuate cross-section to accommodate needle B. Base portion 38 of channel 36 is preferably dimensioned to generally correspond to the outer dimension or contours of needle B such that the needle park material surrounding the base portion substantially encloses the needle B within the needle park.

Referring again to FIGS. 1–3, needle park 32 extends through a circular opening 40 defined in cover sheet 26. Accordingly, in the secured position of needle B, the needle is retained in a prostrate position against cover sheet 26 in general parallel relationship with base panel 22. Such parallel positioning of needle B minimizes the overall girth of retainer 20 thereby facilitating packaging of the retainer within an outer package.

Figure 5:
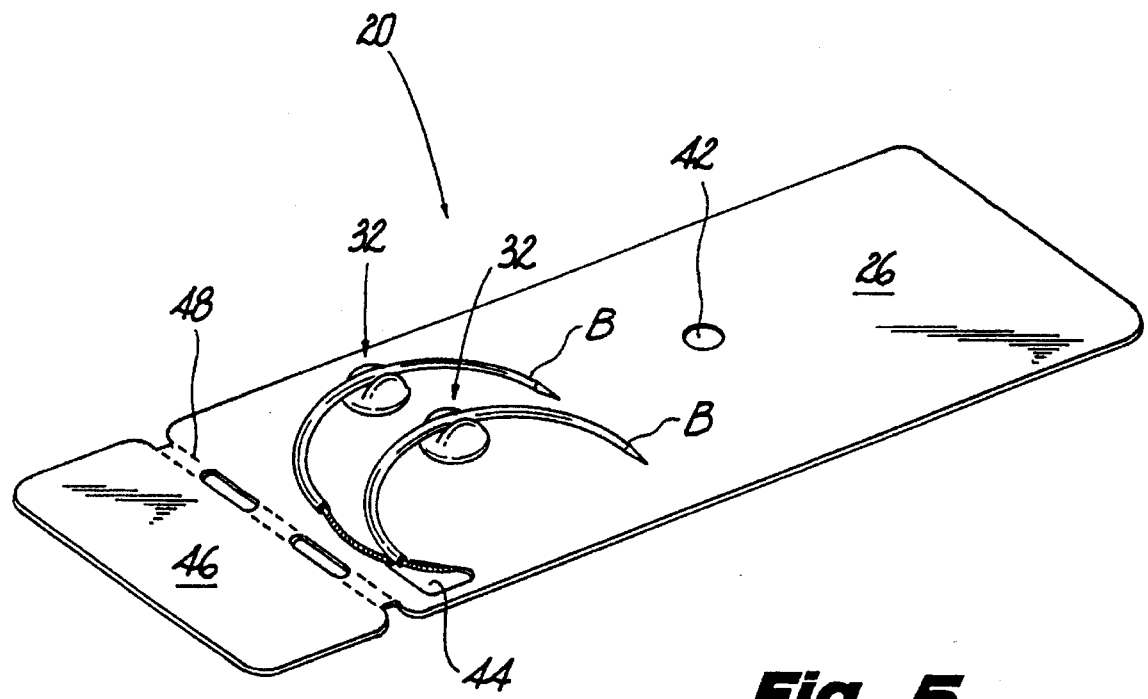
FIG. 5 is a perspective view of the suture retainer of FIG. 1 with two needle parks.

Needle receiving channel 36 defined by transverse members 34 may be substantially straight to facilitate retention of a straight surgical needle. In the alternative, needle receiving channel 36 may be slightly curved to facilitate retention of a curved surgical needle. In the preferred embodiment, needle park 36 is integrally formed with base panel 22. However, it is also within the scope of the present invention for needle park 32 to be an independent component separate from base panel 22. It is also contemplated that retainer 20 may contain several needle parks 32 to accommodate a plurality of surgical needles as shown in FIG. 5 where two needle parks 32 are provided so as to secure the needles of a double armed suture.

Referring now to FIGS. 1 and 2, cover sheet 26 is configured and dimensioned to overlie base panel 22 and is adhesively attached to the base panel 22 along respective peripheral portions thereof to enclose the passageway 24. In a preferred embodiment, cover sheet 26 is adhered to base panel 22 with a hot melt adhesive from Oliver Products of Minneapolis, Minn.

The cover sheet 26 is provided with a vacuum aperture 42 and a suture entrance aperture 44. Vacuum aperture 42 aligns and communicates with the central vacuum receiving section 30 of the molded base panel 22. Similarly, suture entrance aperture 44 aligns and communicates with the suture receiving section 28. Preferably, cover sheet 26 is constructed of a material which is pervious to ethylene oxide sterilizing gas. The preferred material is a spun bonded polyolefin, such as TYVEK™ 1073B available from E.P. DuPont de Nemours & Co.

Referring still to FIGS. 1 and 2, a preferred cover sheet 26 includes a needle cover panel 46 joined to the main section of the cover sheet along doubled perforated score line 48 and openings 50. Needle cover panel 46 is adapted to fold onto needle B retained within the needle park 32 to protect the needle when the retainer is in a secured position.

Suture A may be loaded into retainer 20 by initially folding the suture onto itself to form a first loop and then folding the suture again onto itself to form a second loop. The number of loops required generally depends on the length of the suture to be loaded. Thereafter, the suture portions opposite needle B are inserted through suture entrance aperture 44 in cover sheet 26 and into suture receiving section 28 of base panel 22. A vacuum is applied to the retainer by, e.g., placing a vacuum block (not shown) over vacuum aperture 42 to draw suture A into passageway 24 of base panel 22. The vacuum is applied until needle B is disposed substantially adjacent suture entrance aperture 44. Thereafter, needle B is positioned within needle receiving channel 36 of needle park 32. As an alternative insertion technique, needle B may be positioned within needle park prior to loading suture A. Thereafter, a vacuum may be applied to vacuum aperture 42 to draw the suture A into the retainer.

Retainer 20 with loaded suture A and needle B may be packaged within an outer package. In the case of nonabsorbable sutures, the suture and retainer may be enclosed in a so-called breather pouch suitable for gas sterilization, such as a pouch consisting on one side a sheet of polyolefin (TYVEK™) and on the other side a clear plastic sheet such as polyethylene. The breather pouch is opened by peeling the two sides of the breather pouch apart and opening the needle cover panel to reveal the needle which may be readily grasped to remove the suture from the retainer by a pulling motion.

With synthetic absorbable sutures, the retainer may be packaged in a foil laminate inner envelope which would be further packaged within an outer breather pouch. A preferred inner envelope is disclosed in U.S. patent application Ser. No. 07/718,198, filed Jun. 20, 1991, the contents of which are incorporated herein by reference and includes a top layer having first and second top panels adhered to each other transversely and defining a gripping tab. The top panels are adhered to a bottom panel along respective peripheries thereof to define a pocket for receiving the retainer.

The foregoing inner pouch is preferred, but it will be understood that other types of envelopes such as conventional tearable foil laminate envelopes may be used. It is contemplated that the suture could be sterilized by ethylene oxide permeating through an opening in the pouch which is subsequently sealed and that the peelable pouch itself could be sterilized and maintained sterile in an outer breather pouch in a known matter.

Figure 6:
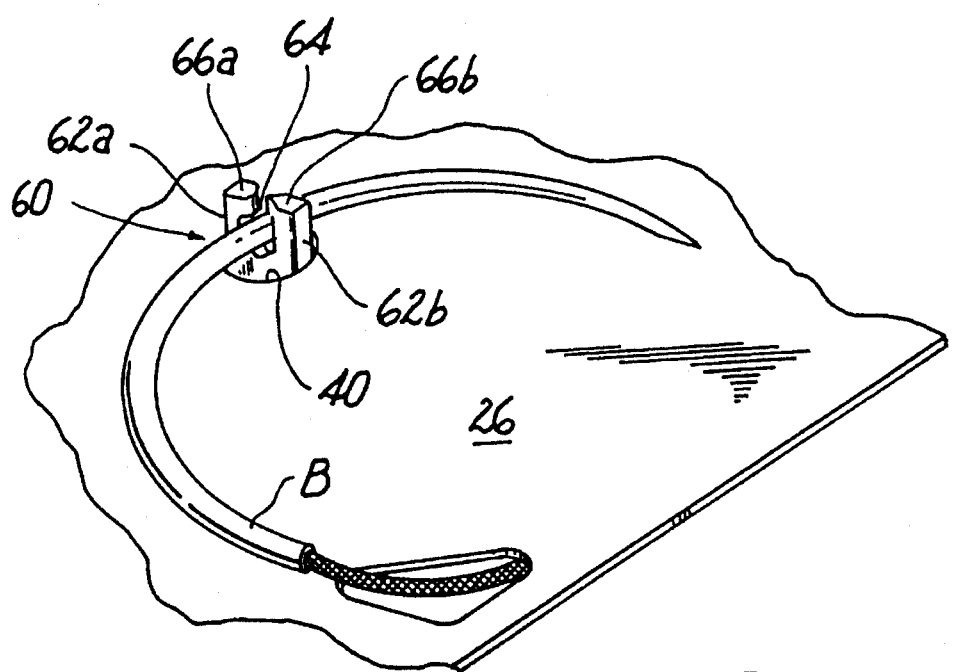
FIG. 6 is a partial perspective view of an alternative needle park to be incorporated in the suture retainer of FIG. 1, including transverse retaining members having generally inwardly extending lip portions to engage the needle.

Referring now to FIG. 6, there is illustrated a partial perspective view of an alternative embodiment of a needle park to be incorporated in retainer 20 of the present invention. Needle park 60 includes two projecting members 62a, 62b extending generally transversely from base panel 22 and through opening 40 defined in cover sheet 26. Projecting members 62a, 62b define a needle receiving channel 64 therebetween to accommodate and retain needle B in a manner similar to the needle park 32 described in connection with the embodiment of FIG. 1. In particular, projecting members 62a, 62b may be dimensioned and positioned to frictionally engage the outer surfaces of needle B. In the alternative, projecting members 62a, 62b may be positioned to define a needle receiving channel 64 of greater dimension so as to permit slight movement of the secured needle B.

Projecting members 62a, 62b also include generally inwardly extending lip portions 66a, 66b formed contiguous with their respective projecting members. Lip portions 66a, 66b are strategically oriented, preferably, in parallel relation to base panel 22 so as to engage needle B to further facilitate retention of the needle within needle park 60 and against cover sheet 26. In particular, lip portions 66a, 66b restrict movement of needle B away from the retainer thereby securing the needle B against the cover sheet. Thus, the combination of transverse members 62a, 62b and lip portions 66a, 66b securely retain the needle within retainer 20.

Figure 7:
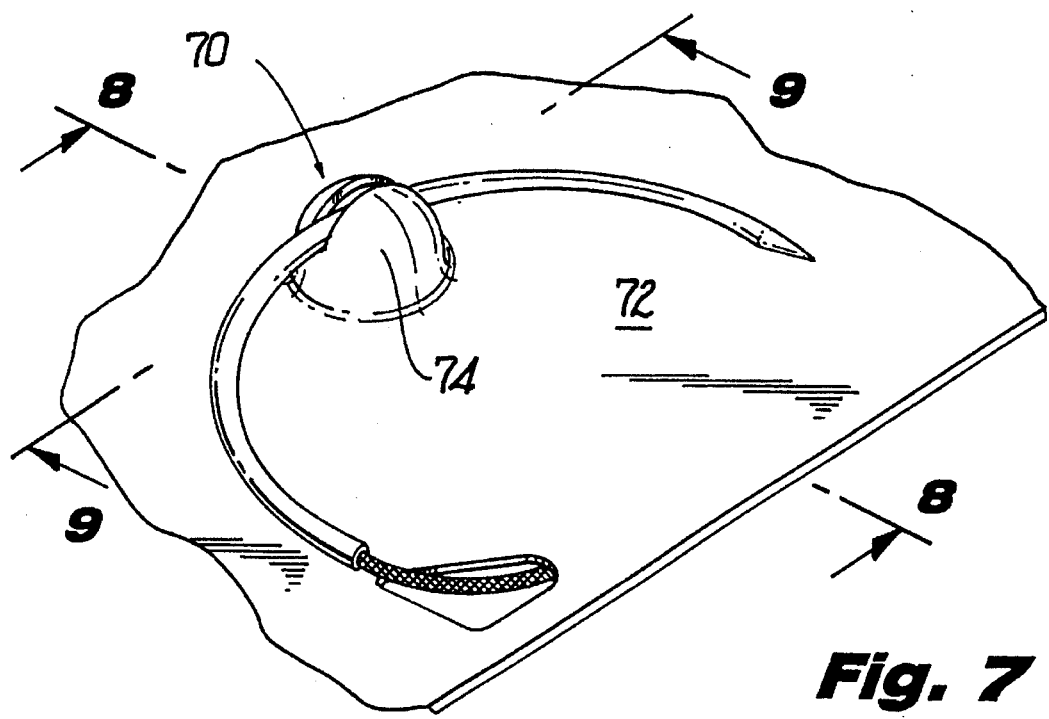
FIG. 7 is a partial perspective view of another alternative needle park, including a molded raised portion having a needle receiving slot therein for retaining the needle.
Figure 8:
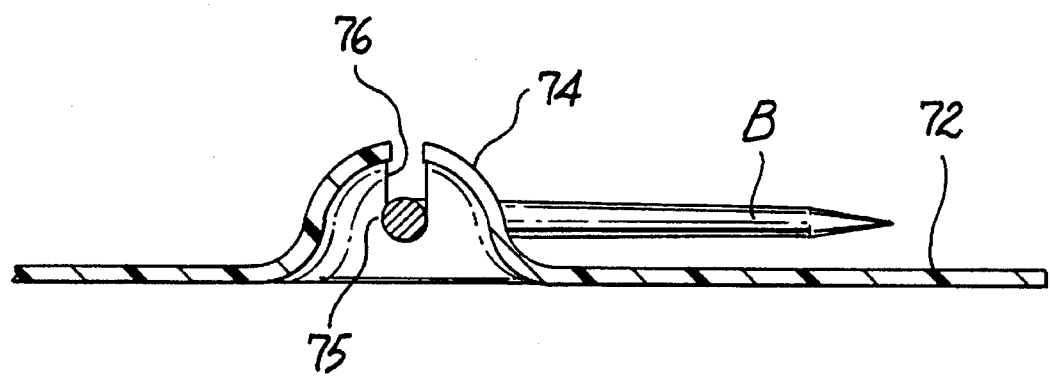
FIG. 8 is a cross-sectional view taken along the lines 8—8 of FIG. 7.
Figure 9:
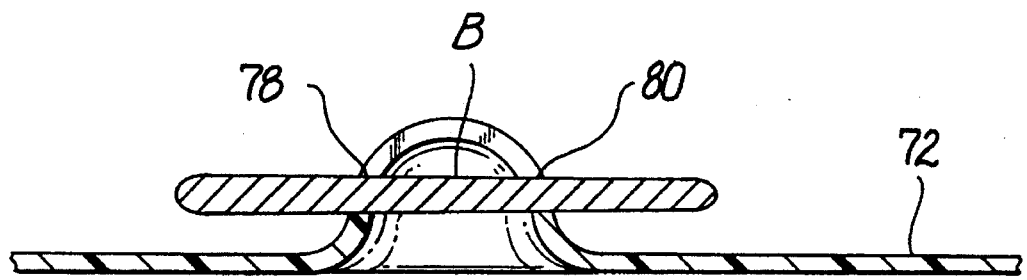
FIG. 9 is a cross-sectional view taken along the lines 9—9 of FIG. 7.
Figure 10:
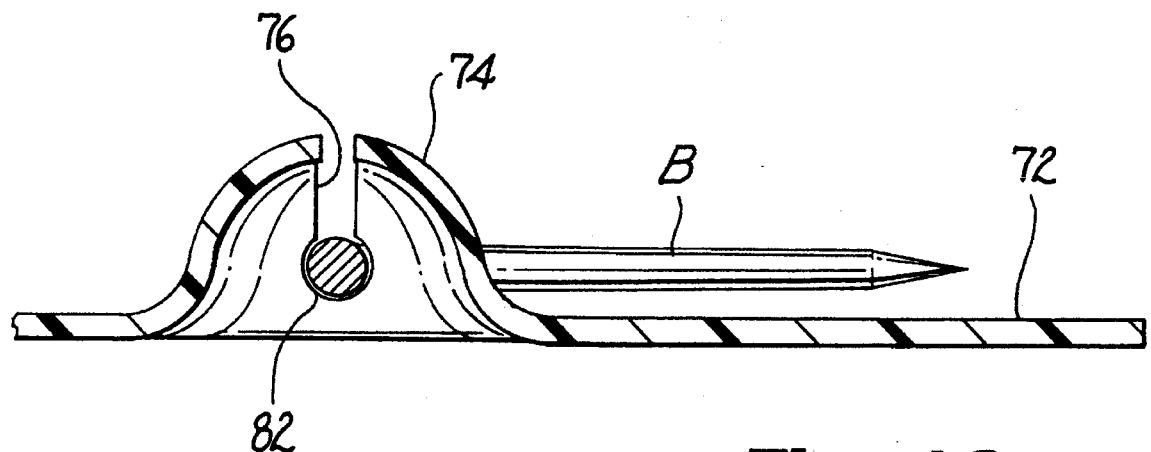
FIG. 10 is a view similar to the cross-sectional view of FIG. 8 illustrating an alternative embodiment of the needle park of FIGS. 7–9, including an arcuate slot portion for accommodating the needle.

Referring now to FIGS. 7–9, there is illustrated another embodiment of a needle park which may be incorporated in the retainer of the present invention. Needle park 70 is preferably integrally formed with a molded substantially planar base panel 72 by, e.g., vacuum molding techniques, to form a hollow raised surface portion 74. Raised surface portion 74 includes a needle receiving slot 76 (FIG. 8) for receiving surgical needle B. Slot 76 can be constructed to have weakened portions 75 to facilitate securement of needle B by means of deformation. Needle B is positioned within slot 76 wherein portions 75 slightly deflect to accommodate the needle. Due to the hollow configuration of the raised surface portion 74, needle B is engaged by contacting portions 78, 80 of the raised surface as shown in the cross-sectional view of FIG. 9. Contacting portions 78, 80 frictionally engage the outer surfaces of needle B to secure the needle within park 70. Needle receiving slot 76 may be substantially straight to receive a straight needle B, or, in the alternative, be slightly arcuately shaped or curved to receive a curved needle B. Needle park 70 may also be provided with a needle receiving slot 76 having an arcuate lower base portion 82 as shown in FIG. 10. In accordance with the embodiment of FIG. 10, the arcuate base portion 82 of needle receiving slot 76 is preferably dimensioned to generally correspond to the outer contour of needle B to substantially surround a peripheral portion of the needle B.

Figure 11:
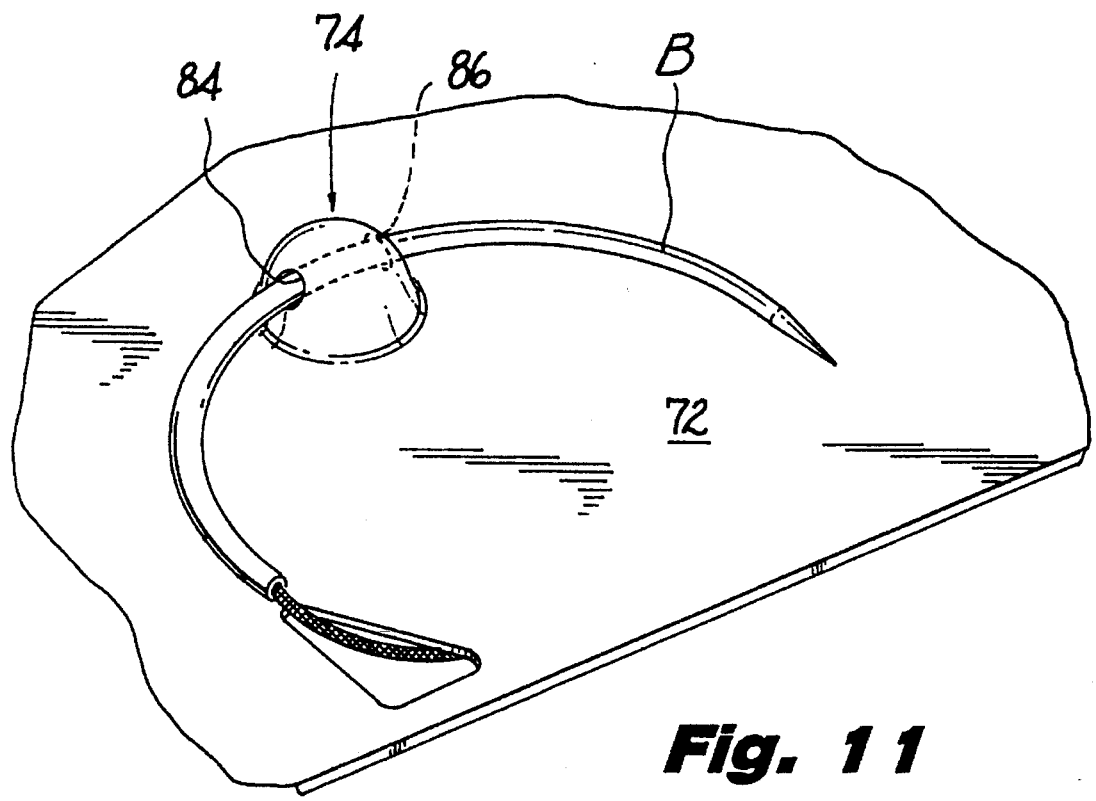
FIG. 11 is a partial perspective view of another alternative embodiment of a needle park, including a molded raised portion having two apertures formed in opposed walls for reception of the needle.

Referring now to FIG. 11, there is illustrated in partial perspective view another embodiment of a needle park of the present invention. This embodiment is substantially similar to the embodiment described in connection with FIG. 10, except that the needle receiving slot 76 has been replaced with two arcuate apertures 84,86 formed on opposed sides of the raised portion. Arcuate apertures 84,86 receive needle B therein. In particular, during securing of needle B within the park, the pointed end of needle B is inserted within aperture 84, passed through the raised portion and out aperture 86 on the opposed side of the raised portion. Preferably, the dimensions of apertures generally correspond to the outer peripheral surface of needle B, and, are preferably dimensioned to frictionally engage the needle. The apertures 84,86 may be in direct alignment with each other to secure a straight surgical needle or, in the alternative, may be slightly offset to accommodate the arcuate configuration of a curved surgical needle B.

The invention in its broader aspects therefore is not limited to the specific embodiments herein shown and described but departures may be made therefrom within the scope of the accompanying claims without departing from the principals of the invention and without sacrificing its chief advantages.

What is claimed is:

1. A suture package which comprises:
   a) a molded base panel having a passageway formed therein for reception of a suture portion;
   b) a cover sheet affixed to the molded base panel to enclose the passageway; and
   c) a needle park extending generally transversely relative to a plane defined by the base panel through an opening formed in the cover sheet for securably engaging a surgical needle, the needle park having a needle receiving channel dimensioned to receive and accommodate the needle therein, the needle relieving channel having a base portion defining a generally arcuate cross section.

2. The suture package according to claim 1, wherein said molded base panel comprises a moldable plastic material.

3. The suture package according to claim 1, wherein said needle holding means is positioned at a proximate midline of said molded base panel.

4. The suture package according to claim 1, wherein said needle holding means comprises at least two said needle parks.

5. The suture package according to claim 1, wherein said cover sheet is constructed of a spun bonded polyolefin.

6. The suture package according to claim 1, wherein said cover sheet includes a suture receiving port to permit access to a suture receiving section of said passageway and a vacuum port aligned with a vacuum receiving section of said passageway.

7. The suture package according to claim 1, further comprising a needle cover panel foldably attached to said cover sheet and adapted to fold onto the needle engaged by said needle holding means.

8. The suture package according to claim 1, wherein the cross-sectional dimension of said base portion of said needle receiving channel generally corresponds to the cross-sectional dimension of the needle.

9. A suture package which comprises:
   a) a molded base panel having a passageway formed therein for reception of a suture portion;
   b) a cover sheet affixed to the molded base panel to enclose the passageway; and
   c) a needle park integrally formed with said molded base panel and extending generally transversely relative to a plane defined by the base panel through an opening formed in the cover sheet for securably engaging a surgical needle, the needle park having a needle receiving channel dimensioned to receive and accommodate the needle therein.

10. The suture package according to claim 9, wherein said needle receiving channel is configured in a manner such that portions of said needle park defining said needle receiving channel frictionally engage a portion of the outer surfaces of the needle to secure the needle to said needle park.

11. The suture package according to claim 10, wherein said needle receiving channel is generally elongated and straight in configuration to facilitate securement of a straight surgical needle.

12. The suture package according to claim 10, wherein said needle receiving channel is generally arcuately-shaped to facilitate securement of a curved surgical needle.

13. The suture package according to claim 9, wherein said molded needle park comprises at least two projecting members extending generally transversely relative to a plane defined by said molded base panel, said projecting members defining said needle receiving channel therebetween, each said projecting member having a lip portion formed contiguous therewith, said lip portions extending generally inwardly towards the center of said needle receiving channel and oriented to engage and retain the needle within said receiving channel.

14. The suture package according to claim 13, wherein said projecting members are positioned to frictionally engage the needle received within said needle receiving channel.

15. The suture package according to claim 13, wherein said lip portions are oriented in general parallel relationship with said plane defined by said molded base panel.

16. The suture package according to claim 13, wherein said lip portions are angularly oriented relative to said plane defined by said molded base panel.

17. A suture retainer for storing at least one suture having a needle attached thereto, which comprises:
   a) a molded base panel having a passageway formed therein for accommodating a suture portion;
   b) a cover sheet affixed to the molded base panel to enclose the passageway; and
   c) at least one needle holding park integrally formed with said molded base panel and extending through at least one opening formed in said cover sheet, said needle park defining a groove therein dimensioned and configured to receive a suture needle and frictionally engage the outer surfaces of the needle to secure the needle therewithin.

18. A needle park according to claim 17, wherein said groove comprises a weakened portion to facilitate securement of a surgical needle.

* * * * *